(12) United States Patent
Wada

(10) Patent No.: US 8,911,091 B2
(45) Date of Patent: Dec. 16, 2014

(54) OPHTHALMOLOGIC APPARATUS HAVING CORNEAL THICKNESS CORRECTION

(75) Inventor: Manabu Wada, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 269 days.

(21) Appl. No.: 13/397,193

(22) Filed: Feb. 15, 2012

(65) Prior Publication Data

US 2012/0218518 A1 Aug. 30, 2012

(30) Foreign Application Priority Data

Feb. 25, 2011 (JP) ................................. 2011-040844
Feb. 2, 2012 (JP) ................................. 2012-021344

(51) Int. Cl.
*A61B 3/107* (2006.01)
*A61B 3/10* (2006.01)
*A61B 3/16* (2006.01)

(52) U.S. Cl.
CPC ................. *A61B 3/165* (2013.01); *A61B 3/107* (2013.01); *A61B 3/1005* (2013.01)
USPC ............ 351/212; 351/205; 351/206; 351/246

(58) Field of Classification Search
CPC .............................. A61B 3/1005; A61B 3/107
USPC ........................................................ 351/212
See application file for complete search history.

(56) References Cited

U.S. PATENT DOCUMENTS

| | | | |
|---|---|---|---|
| 5,471,261 A * | 11/1995 | Yoshizo et al. | ................ 351/210 |
| 5,474,066 A | 12/1995 | Grolman | |
| 5,680,196 A | 10/1997 | Masuda | |
| 6,053,867 A | 4/2000 | Iijima | |
| 2009/0216106 A1 | 8/2009 | Takii | |

FOREIGN PATENT DOCUMENTS

| | | |
|---|---|---|
| CN | 1318343 A | 10/2001 |
| CN | 1494864 A | 5/2004 |
| EP | 2 095 761 A1 | 9/2009 |
| JP | 07-194554 A | 8/1995 |
| JP | 07-323012 A | 12/1995 |
| JP | 08-000562 A | 1/1996 |
| JP | 08-507463 A | 8/1996 |
| JP | 09-084760 A | 3/1997 |
| JP | 09-108185 A | 4/1997 |
| JP | 10-014885 A | 1/1998 |
| JP | 2000-060801 A | 2/2000 |
| JP | 2004-290286 A | 10/2004 |
| JP | 3597274 B2 | 12/2004 |
| JP | 2005-087549 A | 4/2005 |
| JP | 2006-334441 A | 12/2006 |
| JP | 2009-201636 A | 9/2009 |
| JP | 2010-131333 A | 6/2010 |

OTHER PUBLICATIONS

JP 3597264—Dec. 2004—Machine Translation.*
Suzuki, Suzuki S., et al., "Corneal Thickness in an Ophthalmologically Normal Japanese Population." Ophthalmology 112.8 (2005): 1327-1336. Print.*
Jan. 16, 2014 Chinese Official Action in Chinese Patent Appln. No. 201210046698.1.

\* cited by examiner

*Primary Examiner* — Zachary Wilkes
(74) *Attorney, Agent, or Firm* — Fitzpatrick, Cella, Harper & Scinto

(57) ABSTRACT

An ophthalmologic apparatus images a cross-section of the cornea of the eye to be examined based on return light from the eye illuminated with measurement light, measures a corneal thickness from a cornea cross-sectional image of the imaged eye, and corrects the corneal thickness based on the position of the cornea cross-sectional image on an imaging plane.

26 Claims, 11 Drawing Sheets

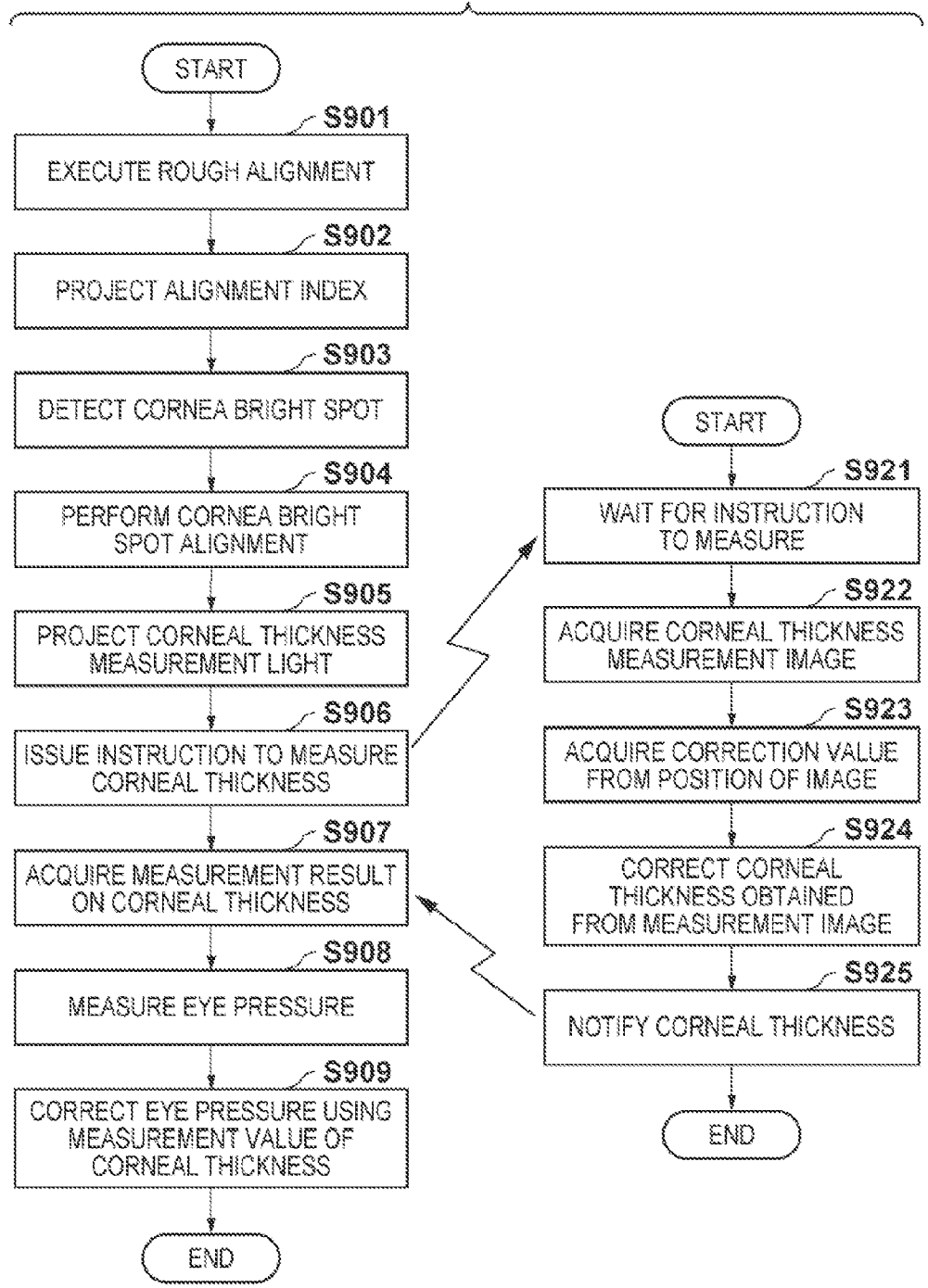

F I G. 10A
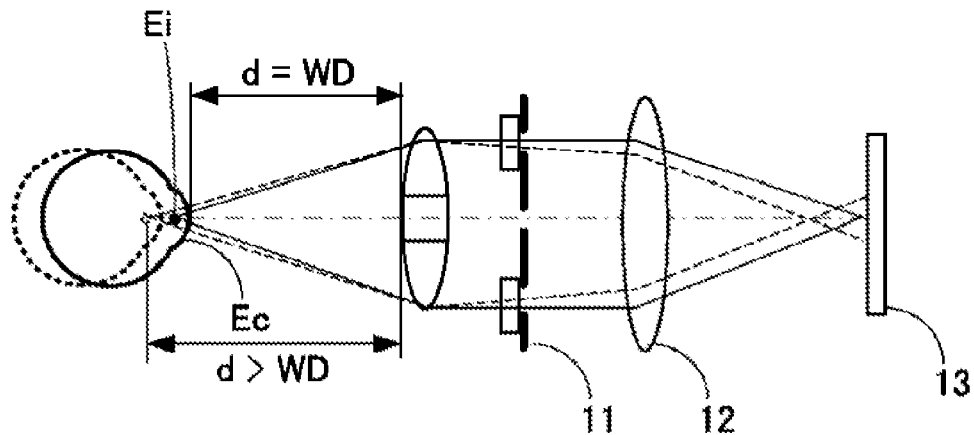
F I G. 10B
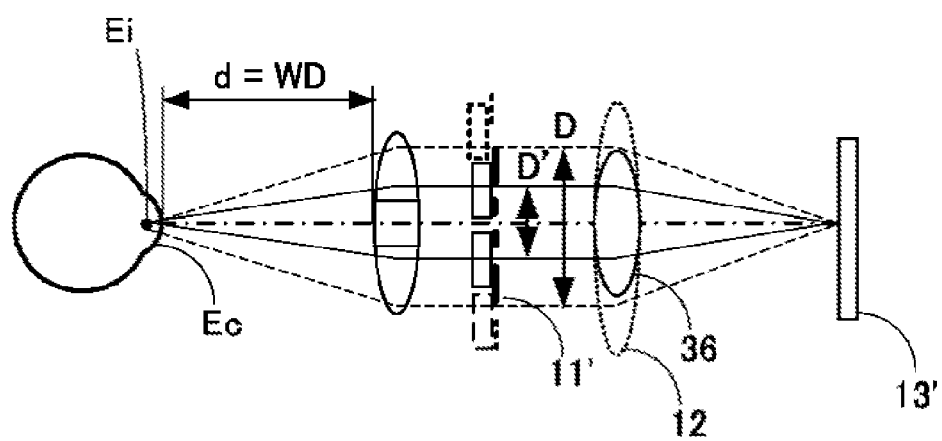
F I G. 10C
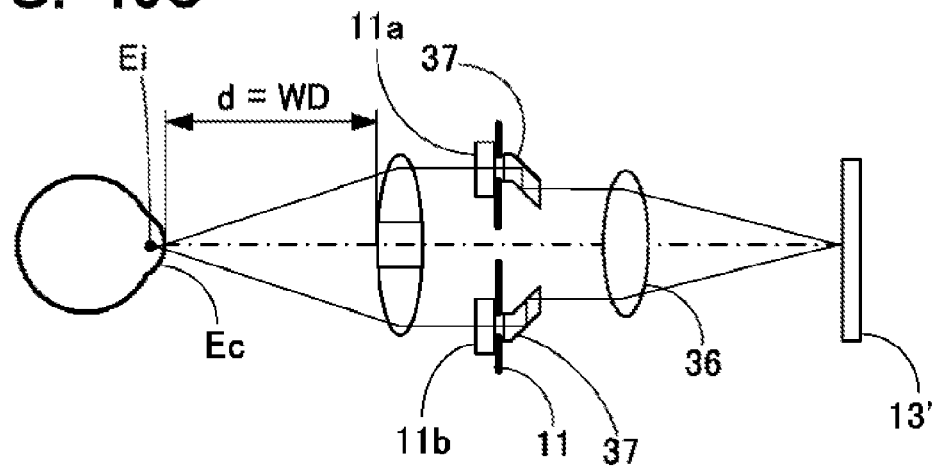

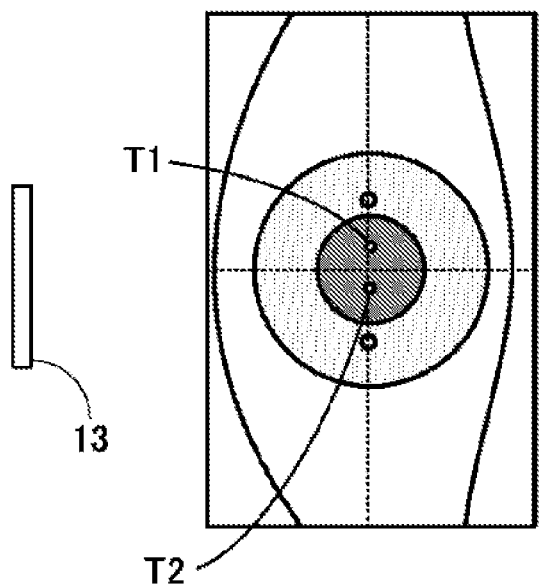 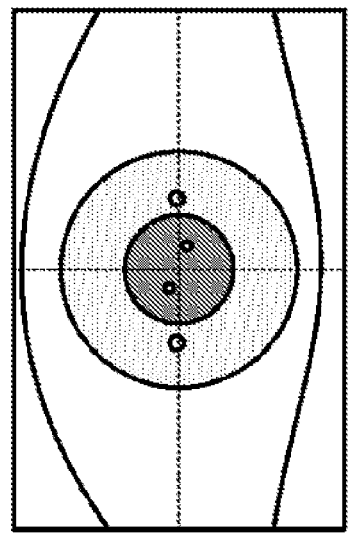
FIG. 11A   FIG. 11B
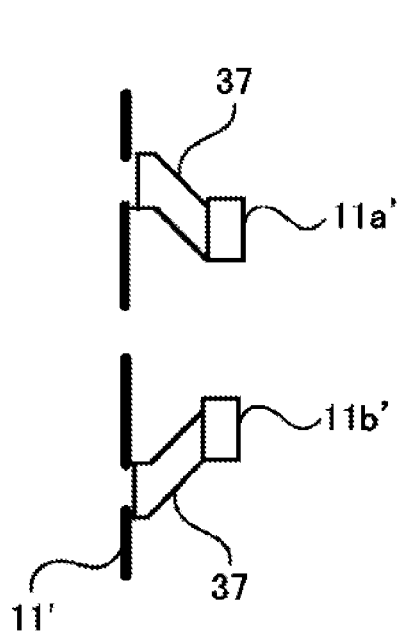 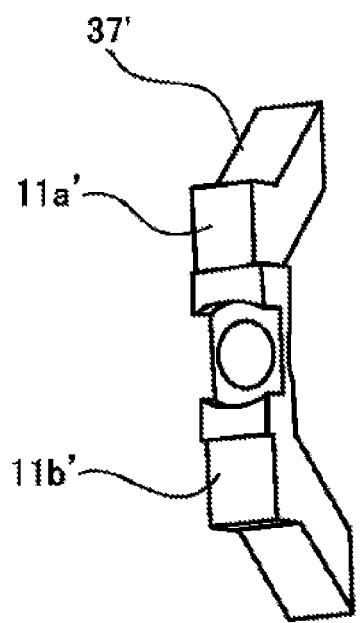
FIG. 12A   FIG. 12B

OPHTHALMOLOGIC APPARATUS HAVING CORNEAL THICKNESS CORRECTION

BACKGROUND OF THE INVENTION

1. Field of the Invention

The present invention relates to an ophthalmologic apparatus having a function of measuring the corneal thickness of an eye to be examined and a control method for the apparatus.

2. Description of the Related Art

In general, an ophthalmologic apparatus designed to measure the corneal thickness of an eye to be examined and the eye pressure performs alignment between the eye to be examined and the apparatus in the vertical direction, the lateral direction, and the operation distance direction (the forward/backward direction, that is, the direction to approach or separate from the eye) with respect to the eye.

A corneal thickness measurement apparatus disclosed in Japanese Patent No. 3597274 performs alignment by using a first projection/light receiving system which performs alignment in the vertical and lateral directions and a second projection/light receiving system which performs alignment in the operation distance direction and is also used for corneal thickness measurement. This apparatus performs alignment in the operation distance direction by using the reflected light of an alignment index projected from the outside of an optical axis facing the eye to be examined to the cornea. When performing alignment in the operation distance direction by using such a system, two projection/light receiving systems are required for alignment and corneal thickness measurement. This makes it impossible to simplify the optical system of the apparatus, and hence leads to increases in the size and cost of the apparatus.

In this case, according to an alignment scheme of a non-contact eye pressure meter disclosed in Japanese Patent Laid-Open No. 2006-334441, an apparatus includes one projection system (shared for alignment and corneal thickness measurement) and two light receiving systems (one of which is a light receiving system for measuring a corneal thickness, which is arranged at a position outside an optical axis facing the eye to be examined). This apparatus performs alignment in the vertical direction, the lateral direction, and the operation distance direction. In this case, a cornea bright spot image is an image that is formed when the cornea of the eye to be examined is illuminated with an alignment index and the reflected light is received from an optical axis facing the eye through a prism.

In this case, when performing alignment by using cornea bright spot images, the operation distance (the distance between the eye to be examined and the apparatus in the forward/backward direction) varies depending on not only alignment errors, but also on the differences in curvature between the surfaces of the corneas. For this reason, when measuring corneal thicknesses, the angle of the optical axis of the light receiving system that receives scattered light from the corneas and the optical path lengths to the light receiving element varies. As a consequence, blur occurs in scattered light from the cornea imaged on the light receiving element, resulting in a failure to perform accurate corneal thickness measurement.

SUMMARY OF THE INVENTION

The present invention has been made in consideration of the above problems, and allows an ophthalmologic apparatus having a function of measuring the corneal thickness of an eye to be examined to accurately measure a corneal thickness with an optical system having a simple arrangement.

According to one aspect of the present invention, there is provided an ophthalmologic apparatus comprising: an imaging unit configured to image a cross-section of a cornea of an eye to be examined based on return light from the eye illuminated with measurement light; a measurement unit configured to measure a corneal thickness from a cornea cross-sectional image of the eye imaged by the imaging unit; and a correction unit configured to correct the corneal thickness based on a position of the cornea cross-sectional image on an imaging plane of the imaging unit.

According to another aspect of the present invention, there is provided a control method for an ophthalmologic apparatus, the method comprising: an imaging step of imaging, by using an imaging unit, a cross-section of a cornea of an eye to be examined based on return light from the eye illuminated with measurement light; a measurement step of measuring a corneal thickness from a cornea cross-sectional image of the eye imaged in the imaging step; and a correction step of correcting the corneal thickness based on the position of the cornea cross-sectional image on an imaging plane of the imaging unit.

Furthermore, according to another aspect of the present invention, there is provided an ophthalmologic apparatus including: an alignment index projection system which projects an alignment index to a cornea of an eye to be examined; a plurality of aperture stops which are arranged at symmetric positions with respect to an optical axis facing the eye at a predetermined distance from each other so as to make light beams of cornea reflection images using the alignment index pass through; a deflection unit configured to, arranged before or after the plurality of aperture stops, deflect light beams in different directions; an imaging lens which images the deflected light beams on an imaging plane of an imaging unit; and optical members which are arranged on optical paths of light beams passing through the aperture stops and change a distance between light beams which corresponds to the predetermined distance between the aperture stops.

Further features of the present invention will become apparent from the following description of exemplary embodiments with reference to the attached drawings.

BRIEF DESCRIPTION OF THE DRAWINGS

FIG. 9 is a flowchart showing the operation of an ophthalmologic apparatus according to an embodiment;

FIG. 10A is a view showing an imaging relationship based on differences in WD;

FIG. 10B is a view for explaining alignment accuracy based on differences in the distance between aperture stops;

FIG. 10C is a view showing how optical members are used to cope with a reduction in size while maintaining alignment accuracy;

FIGS. 11A and 11B are views showing the positional relationship between cornea bright spots based on differences in WD;

FIG. 12A is a view showing a different arrangement of aperture stops, optical members, and prisms; and FIG. 12B is a view showing an arrangement obtained by integrating the aperture stops.

DESCRIPTION OF THE EMBODIMENTS

A preferred embodiment of the present invention will be described below with reference to the accompanying drawings.

First Embodiment

Figure 1:
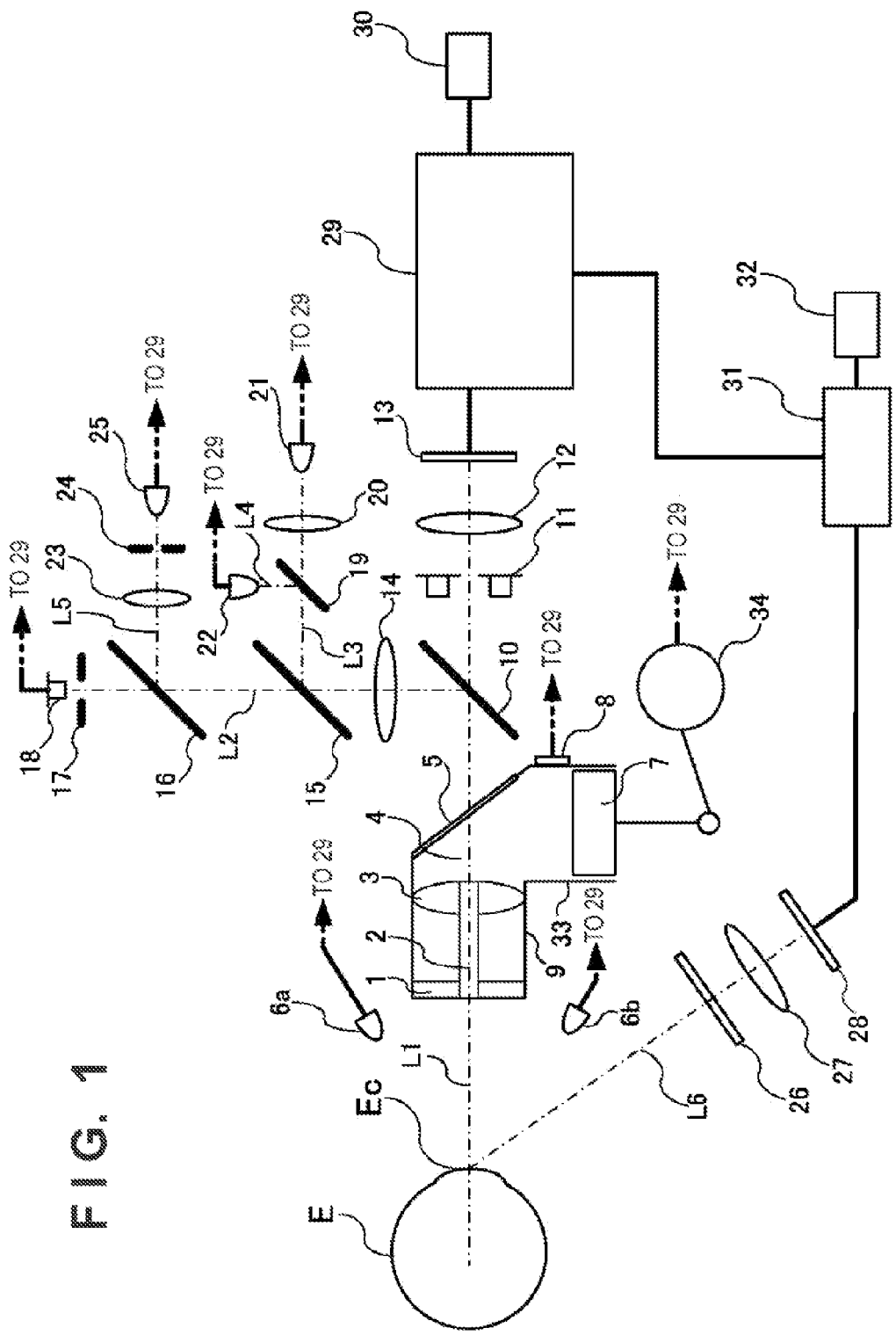
FIG. 1 is a block diagram showing an example of the arrangement of the measuring unit of an ophthalmologic apparatus according to an embodiment.

FIG. 1 is a block diagram showing an example of the arrangement of a measuring unit in an ophthalmologic apparatus according to this embodiment. The ophthalmologic apparatus of the embodiment has both the functions of a corneal thickness measurement apparatus that measures the corneal thickness of an eye to be examined and a non-contact eye pressure meter that measures the eye pressure.

A plane parallel glass 1 and an objective lens 3 are arranged on an optical axis L1 facing a cornea Ec of an eye E to be examined. A nozzle 2 is provided on the center axis of the optical axis L1. An air chamber 4, an observation window 5, a dichroic mirror 10, a prism stop 11, an imaging lens 12, and an imaging element 13 are sequentially arranged behind the nozzle 2. These components constitute an observation system and an alignment detection system for the eye E.

An objective lens barrel 9 supports the plane parallel glass 1 and the objective lens 3. Extraocular illumination light sources 6a and 6b for illuminating the eye E are arranged outside the objective lens barrel 9. The extraocular illumination light sources 6a and 6b are arranged at symmetric positions with respect to the optical axis L1. The dichroic mirror 10 transmits light with the wavelength emitted from the extraocular illumination light sources 6a and 6b and reflects part of light with the wavelength emitted from an LED light source (to be described later) used for both eye pressure measurement and alignment.

Figure 2A:
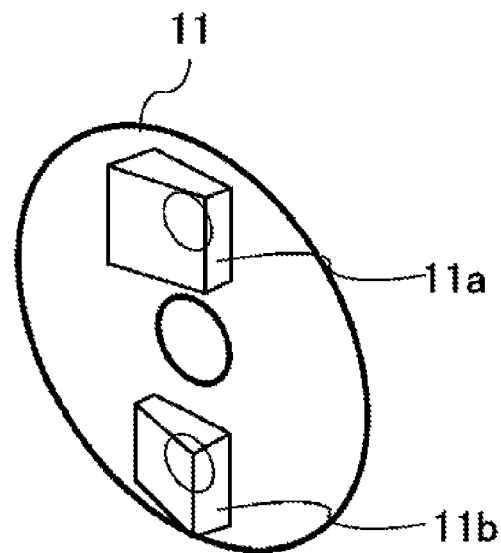
FIG. 2A is a view showing a prism stop 11.

As shown in FIG. 2A, the prism stop 11 has three apertures. The upper and lower apertures are respectively provided with prisms 11a and 11b for polarizing light beams in different lateral directions. In practice, these apertures are arranged laterally, and the prisms 11a and 11b deflect light beams vertically. Assume, however, that in the following description, these apertures are arranged vertically. In addition, the upper and lower apertures of the prism stop 11 are provided with filters having spectral characteristics of absorbing wavelength light from the extraocular illumination light sources 6a and 6b and transmitting wavelength light from the LED light source used for both eye pressure measurement and alignment. Note that the number of apertures is not limited to two but may be three or more. On the other hand, the aperture in the center of the prism stop 11 is provided with a filter which absorbs wavelength light from the LED light source used for both eye pressure measurement and alignment and transmits wavelength light from the extraocular illumination light sources 6a and 6b.

A relay lens 14, a half mirror 15, a dichroic mirror 16, an aperture 17, and a light receiving element 18 are arranged on an optical axis L2 of the dichroic mirror 10 in the reflecting direction. They constitute a corneal deformation detection system which detects a change in the amount of corneal reflex light. The dichroic mirror 16 has characteristics of transmitting near-infrared wavelengths and reflecting visible light wavelengths.

A half mirror 19, a projection lens 20, and an LED light source 21 used for both eye pressure measurement and alignment described above are arranged on an optical axis L3 of the half mirror 15 in the reflecting direction. They constitute an eye pressure measurement light projection system and an alignment index projection system. A visual fixation light source 22, which presents a fixation lamp for the visual fixation of the eye E, is placed on an optical axis L4 of the half mirror 19 in the reflecting direction.

Figure 2B:
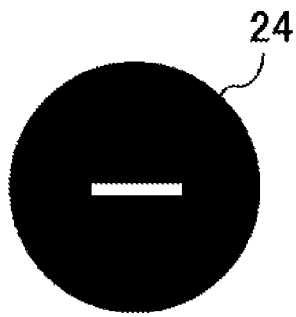
FIG. 2B is a view showing a slit plate 24.

A projection lens 23, a slit plate 24, and an LED light source 25 used for the measurement of a corneal thickness are arranged on an optical axis L5 of the dichroic mirror 16 in the reflecting direction. As shown in FIG. 2B, the slit plate 24 serves as a rectangular stop which is longer in a direction perpendicular to the drawing surface.

A filter 26, which transmits light in the corneal scattered light wavelength region, which is emitted from the LED light source 25, an imaging lens 27, and an imaging element 28 are arranged on an optical axis L6 of the eye E in an obliquely downward direction. They constitute a corneal thickness measurement optical system. The optical axes L1 and L6 intersect at the corneal vertex of the cornea Ec of the eye to be examined. The slit plate 24, the cornea Ec, and the imaging element 28 are almost conjugate to each other. A corneal thickness calculation unit 31 is connected to the output of the imaging element 28. A corneal thickness correction data unit 32 is connected to the corneal thickness calculation unit 31.

A piston 7, which is driven by a solenoid 34, is slidably fitted in a cylinder 33 in the air chamber 4. The nozzle 2, the air chamber 4, the solenoid 34, and the piston 7 constitute a pressurizing unit. A pressure sensor 8 for monitoring the internal pressure is placed in the air chamber 4.

In addition, a control unit 29 controls the overall apparatus. The imaging element 13, a measurement start switch 30 for starting measurement, and the corneal thickness calculation unit 31 are connected to the control unit 29. Furthermore, the extraocular illumination light sources 6a and 6b, the light receiving element 18, the LED light source 21 used for both eye pressure measurement and alignment, the visual fixation light source 22, the LED light source 25 for corneal thickness measurement, the pressure sensor 8, and the solenoid 34 are connected to the control unit 29.

In addition, the measuring unit incorporating the optical system in FIG. 1 is mounted on a stage unit (not shown), and is driven by a motor in three axial directions including the direction of the optical axis L1 of the eye E and directions perpendicular to the optical axis L1.

The operation of the ophthalmologic apparatus according to this embodiment will be described next with reference to the flowchart of FIG. 9. Note that the processing shown in FIG. 9 is the processing executed by the control unit 29 and the corneal thickness calculation unit 31. During measurement, the control unit 29 turns on the visual fixation light source 22 to make the eye E perform visual fixation to the visual fixation light source 22. In this state, when an examiner presses the measurement start switch 30, the control unit 29 positions the eye to be examined to the apparatus main body. This positioning operation is performed in two steps including rough alignment and alignment using a cornea bright spot. First of all, the control unit 29 performs rough alignment (step S901). More specifically, the control unit 29 turns on the extraocular illumination light sources 6a and 6b to illuminate the anterior eye part of the eye E with illumination light beams from the light sources. The illumination light beams reflected and scattered by the anterior eye part are almost collimated by the plane parallel glass 1 and the objective lens 3, pass through the observation window 5, the dichroic mirror 10, and the aperture in the center of the prism stop 11, and form an image on the imaging element 13 through the imaging lens 12.

The control unit 29 detects the pupil from the anterior eye part image, obtained from the imaging element 13, by performing binarization processing using a proper threshold, and obtains the pupil center. The control unit 29 then moves the measuring unit by driving the stage such that the relative positions of the optical axis L1 and the pupil of the eye to be examined fall within an allowable range within a plane in an x-y direction perpendicular to the optical axis L1, thereby performing rough alignment. In this embodiment, the optical system for performing rough alignment in the above manner will be referred to as the first alignment optical system. Assume that the first alignment optical system includes the components ranging from the plane parallel glass 1 to the imaging element 13 located on the optical axis denoted by reference symbol L1 and extending to the cornea and the extraocular illumination light sources 6a and 6b.

When completing the rough alignment using the first alignment optical system described above, the control unit 29 performs alignment using a cornea bright spot (steps S902 to S904). The control unit 29 turns on the LED light source 21 to project an alignment index on the cornea (step S902). A light beam from the LED light source 21 temporarily forms an image inside the nozzle 2 through the projection lens 20, the half mirror 19, the half mirror 15, the relay lens 14, the dichroic mirror 10, and the objective lens 3. Then, the image reaches the eye E, and is reflected by the cornea Ec. The light beam reflected by the cornea Ec is focused by the plane parallel glass 1 and the objective lens 3. After the light beam passes through the observation window 5, several percent of the light beam passes through the dichroic mirror 10. Of the light beams passing through the dichroic mirror 10, only the light beams passing through the prisms 11a and 11b provided for the corresponding apertures of the three apertures of the prism stop 11 form images on the imaging element 13 through the imaging lens 12. At this time, the prisms 11a and 11b deflect the light beams passing through the upper and lower apertures of the prism stop 11 in the rear side direction and front side direction with respect to the drawing surface. Consequently, light from the LED light source 21 forms two divided cornea bright spot images on the imaging element 13. The positional relationship between these images changes depending on the relative positions of the eye E and measuring unit. The control unit 29 detects the positional relationship between these two divided cornea bright spot images from the images obtained by the imaging element 13, thereby allowing the apparatus to determine the positional relationship between the eye E and the measuring unit (step S903). In this case, alignment using these cornea bright spot images will be referred to as cornea bright spot alignment.

An optical system for executing cornea bright spot alignment as described above will be referred to as a second alignment optical system. The second alignment optical system therefore includes an alignment index projection system along the optical axes L3, L2, and L1, which is used to project an alignment index onto the cornea of the eye to be examined, and an alignment index detection system along the optical axis L1, which is used to detect the alignment index projected on the cornea. In addition, the first alignment optical system and the second alignment optical system have the arrangement on the optical axis L1 in common.

FIGS. 8A to 8D each show the two cornea bright spot images captured by the imaging element 13 when executing cornea bright spot alignment. In this case, reference symbols T1(x1, y1) and T2(x2, y2) respectively denote two cornea bright spot images. On the imaging element 13, the cornea bright spot image T1(x1, y1) and the cornea bright spot image T2(x2, y2) are respectively located on the front side and rear side with respect to the drawing surface. In addition, central coordinates T(xt, yt) of a line segment connecting the two cornea bright spot images T1(x1, y1) and T2(x2, y2) coincide with the optical axis L1. The center of the cornea Ec is indicated by an intersection point C(x0, y0) of the x- and y-coordinates.

Figure 8B:
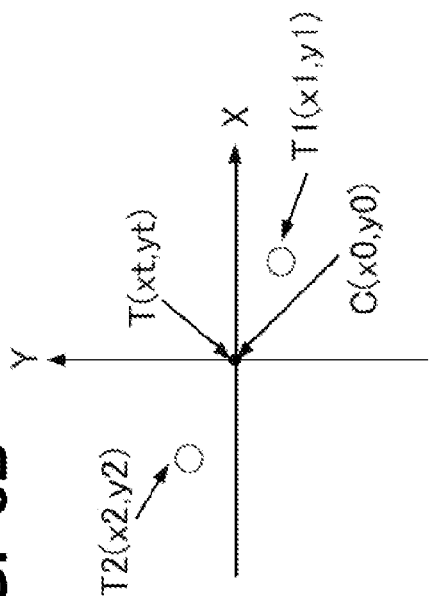
FIGS. 8A to 8D are graphs for explaining the relationship between operation distances and the two cornea bright spot images captured in cornea bright spot alignment.
Figure 8D:
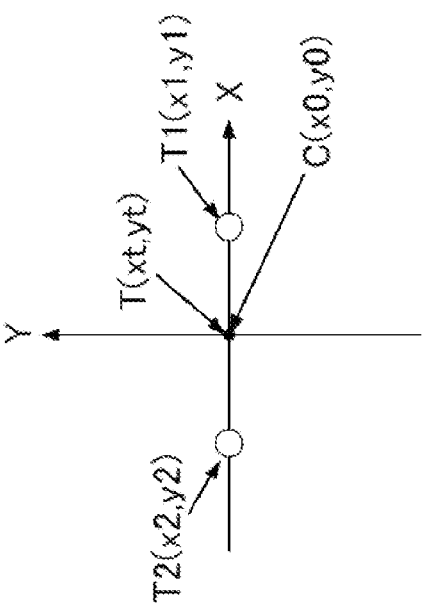
Figure 8A:
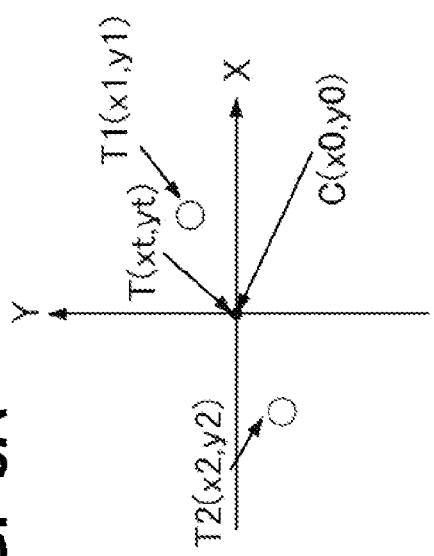
Figure 8C:
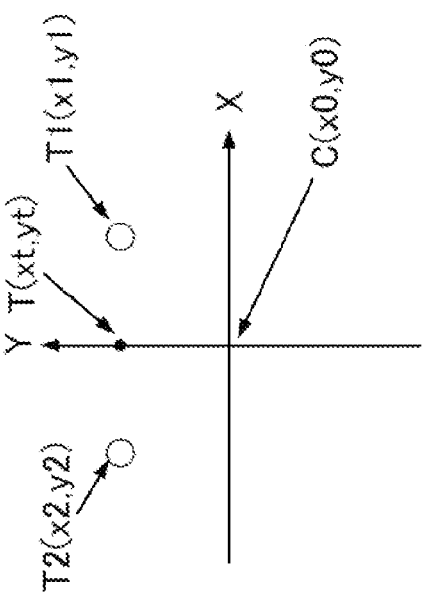

FIG. 8A shows a case in which the operation distance between the eye E and the measuring unit is larger than a predetermined distance. FIG. 8B shows a case in which the operation distance between the eye E and the measuring unit is smaller than a predetermined distance. FIG. 8C shows a case in which the positional relationship between the eye E and the measuring unit is shifted in the y direction. FIG. 8D shows a case in which cornea bright spot alignment is complete between the eye E and the measuring unit.

If, for example, the operation distance between the eye E and the measuring unit is larger than the predetermined distance, the apparatus moves the cornea bright spot image T2(x2, y2) downward, and the cornea bright spot image T1(x1, y1) upward, as shown in FIG. 8A. In contrast, if the operation distance between the eye E and the measuring unit is smaller than the predetermined distance, the apparatus moves the cornea bright spot image T2(x2, y2) upward, and the cornea bright spot image T1(x1, y1) downward, as shown in FIG. 8B. Assume that the images are shifted in the y direction in the positional relationship between the eye E and the measuring unit. In this case, as shown in FIG. 8C, y1 and y2 coincide with each other and x0 and xt coincide with a center c(x0, y0) of the cornea Ec, but y0 and yt differ from each other. If cornea bright spot alignment is complete between the eye E and the measuring unit, the two cornea bright spot images T1(x1, y1) and T2(x2, y2) are located at positions equidistant from the center of the cornea Ec and juxtaposed on the x-axis, with the central coordinates T1(x1, yt) coinciding with the center C(x0, y0) of the cornea Ec, as shown in FIG. 8D.

In this manner, in cornea bright spot alignment, the control unit 29 obtains alignment shifts between the eye E and the measuring unit like those shown in FIGS. 8A to 8C, and drives the stage to set the positions of the cornea bright spot images to those shown in FIG. 8D (step S904).

Figure 3:
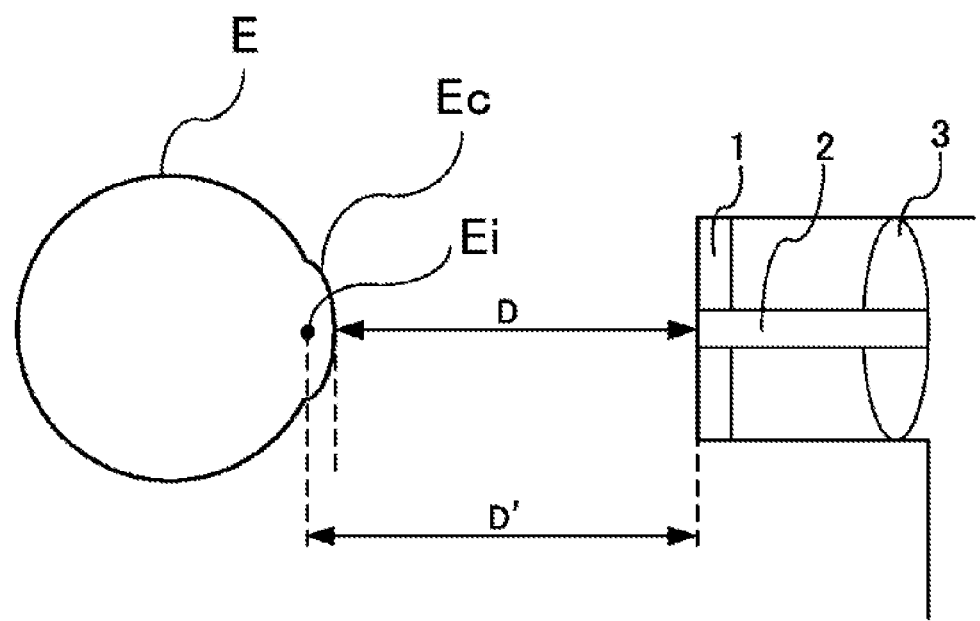
FIG. 3 is a view showing the distance D between the corneal vertex of a cornea Ec and the distal end portion of a nozzle in cornea bright spot alignment.

Note that when the control unit 29 performs cornea bright spot alignment, a distance D from the corneal vertex of the cornea Ec to the distal end portion of the nozzle 2 changes due to differences in the curvature of the surface of the cornea Ec (the curvature of the surface of the cornea Ec will be referred to as a corneal curvature), as shown in FIG. 3. When performing cornea bright spot alignment, the apparatus operates to make a distance D' from a virtual image Ei, formed when the light beam projected from the LED light source 21 is reflected by the cornea Ec, to the distal end portion of the nozzle 2 constant regardless of the corneal curvature of the eye E. This is because the distance D from the corneal vertex of the cornea Ec to the distal end portion of the nozzle 2 changes with changes in corneal curvature.

When the cornea bright spot alignment is complete in the above manner, the apparatus measures the corneal thickness (steps S905 to S907). When measuring the corneal thickness, the control unit 29 turns off the LED light source 21 and turns on the LED light source 25 for corneal thickness measurement (step S905). The control unit 29 issues an instruction to the corneal thickness calculation unit 31 to calculate the corneal thickness (step S906).

In corneal thickness measurement, the slit light formed by illuminating the slit plate 24 using the LED light source 25 passes through the projection lens 23, the dichroic mirror 16, the half mirror 15, the relay lens 14, the dichroic mirror 10, and the nozzle 2 and forms an image on the cornea Ec. The slit light imaged on the cornea Ec is scattered by the cornea Ec. The scattered light passes through the filter 26 and the imaging lens 27 arranged along the optical axis L6, and is imaged by the imaging element 28. The corneal thickness calculation unit 31 calculates the corneal thickness by using the image data output from the imaging element 28 and the data stored in the corneal thickness correction data unit 32. Upon receiving the corneal thickness measurement result from the corneal thickness calculation unit 31 (step S907), the control unit 29 starts measuring the eye pressure (step S908).

As described above, the apparatus calculates the corneal thickness by using:
the projection optical system (the optical system along L5→L2→L1) which projects corneal thickness measurement light for corneal thickness measurement onto the cornea of the eye to be examined by making the first and second alignment optical system have a portion on the optical axis (optical axis L1) extending to the cornea in common; and
the light receiving optical system (the optical system along the optical axis L6 outside the optical axis L1) which images scattered light from the cornea, obtained when the projection optical system projects the corneal thickness measurement light onto the cornea, outside the optical axis to form an image corresponding to the corneal thickness of the cornea.

In eye pressure measurement, the apparatus turns on the LED light source 21 (turns off the LED light source 25), and deforms the cornea by blowing an air current from the nozzle 2 against the cornea of the eye to be examined. The apparatus then measures the eye pressure value by detecting a change in reflected light corresponding to the deformation of the cornea. Eye pressure measurement will be described in more detail below. The control unit 29 drives the solenoid 34. The piston 7 pushed upward by the solenoid 34 then compresses the air in the air chamber 4 to blow the air in the form of a pulse from the nozzle 2 against the cornea Ec of the eye E. The cornea Ec starts to gradually deform in accordance with the strength of air.

At this time, the light receiving element 18 receives the light beam emitted from the LED light source 21 and reflected by the cornea Ec through the aperture 17. The aperture 17 is disposed so as to be almost conjugate to the LED light source 21 when a curvature radius R of the cornea Ec of the eye to be examined is almost infinite. For this reason, as the corneal curvature radius R increases owing to air blown in the form of a pulse, the amount of light received by the light receiving element 18 increases. When the corneal curvature radius R becomes almost infinite, that is, the cornea Ec becomes almost flat, the amount of light received reaches its peak value. The light receiving element 18 detects the peak value when the cornea Ec is made to have a flat surface by the air blown in the form of a pulse. The control unit 29 calculates the eye pressure value of the eye E from the peak value of the light receiving element 18 and the value of the pressure sensor 8 at the corresponding time. Note that when calculating the eye pressure value of the eye E, the control unit 29 obtains the final eye pressure value upon considering the corneal thickness measurement result calculated by the corneal thickness calculation unit 31, that is, correcting the eye pressure measured based on the corneal thickness measurement result (step S909).

The above optical system for measuring the eye pressure of the eye to be examined is called an eye pressure measurement optical system in this embodiment. This eye pressure measurement optical system includes:
an optical system (an optical system along LED light source 21→L3→L2→L1) which makes the first and second alignment optical systems has a portion on the optical axis L1 in common and projects eye pressure measurement light for the measurement of the eye pressure of the eye to be examined onto the eye to be examined; and
an optical system (an optical system along L1→L2→light receiving element 18) which detects reflected light of the eye pressure measurement light from the cornea.

The calculation of a corneal thickness by the corneal thickness calculation unit 31 and the corneal thickness correction data unit 32 in the above ophthalmologic apparatus according to this embodiment will be described with reference to FIGS. 4 to 7 and 9.

The corneal thickness calculation unit 31 waits for an instruction to measure a corneal thickness from the control unit 29 (step S921). Upon receiving an instruction to measure a corneal thickness from the control unit 29, the corneal thickness calculation unit 31 acquires an image for the measurement of a corneal thickness from the imaging element 28 (step S922).

Figure 4:
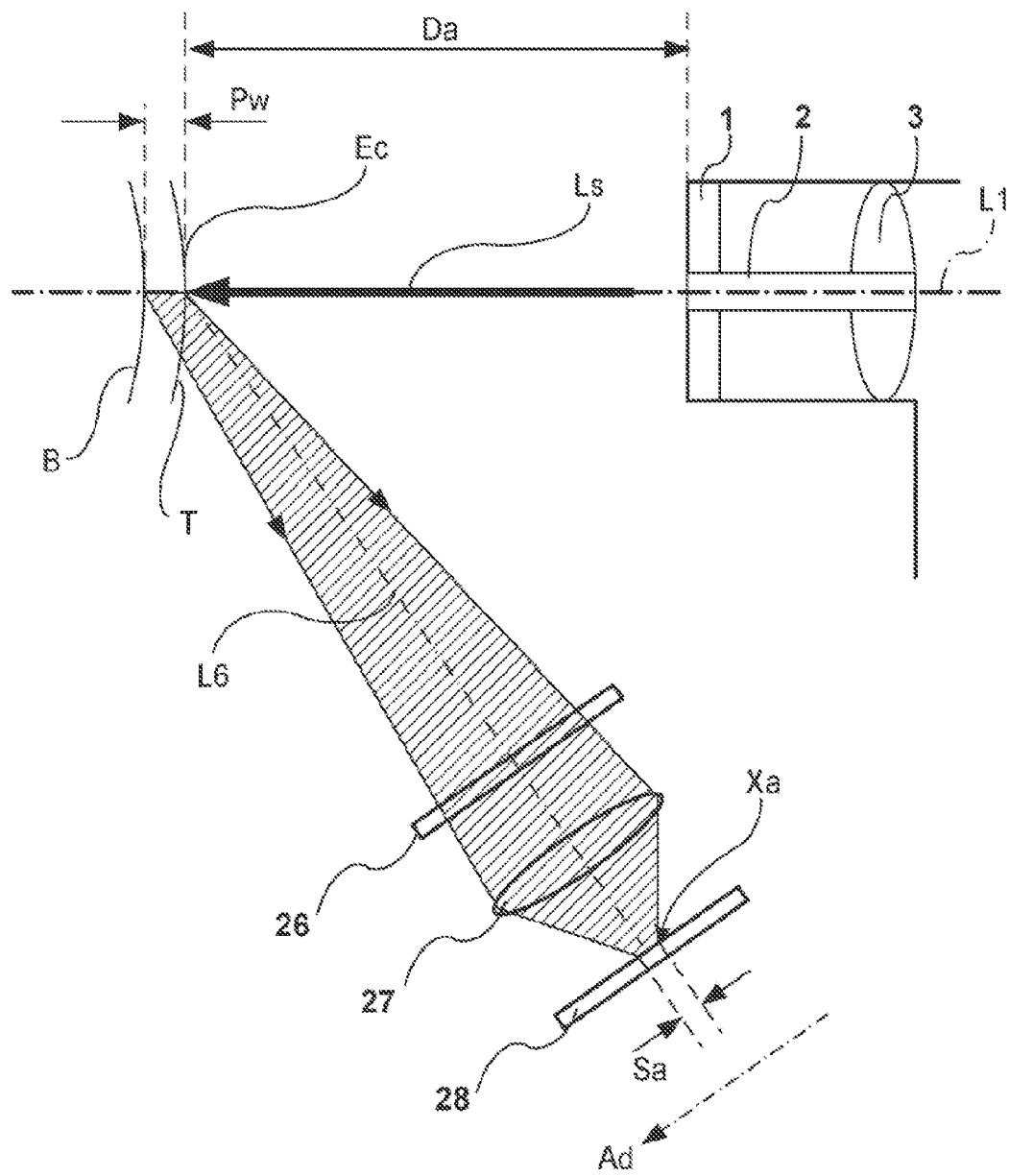
FIG. 4 is a view showing imaging of scattered light from the cornea Ec with an average corneal curvature radius onto an imaging element 28.
Figure 5:
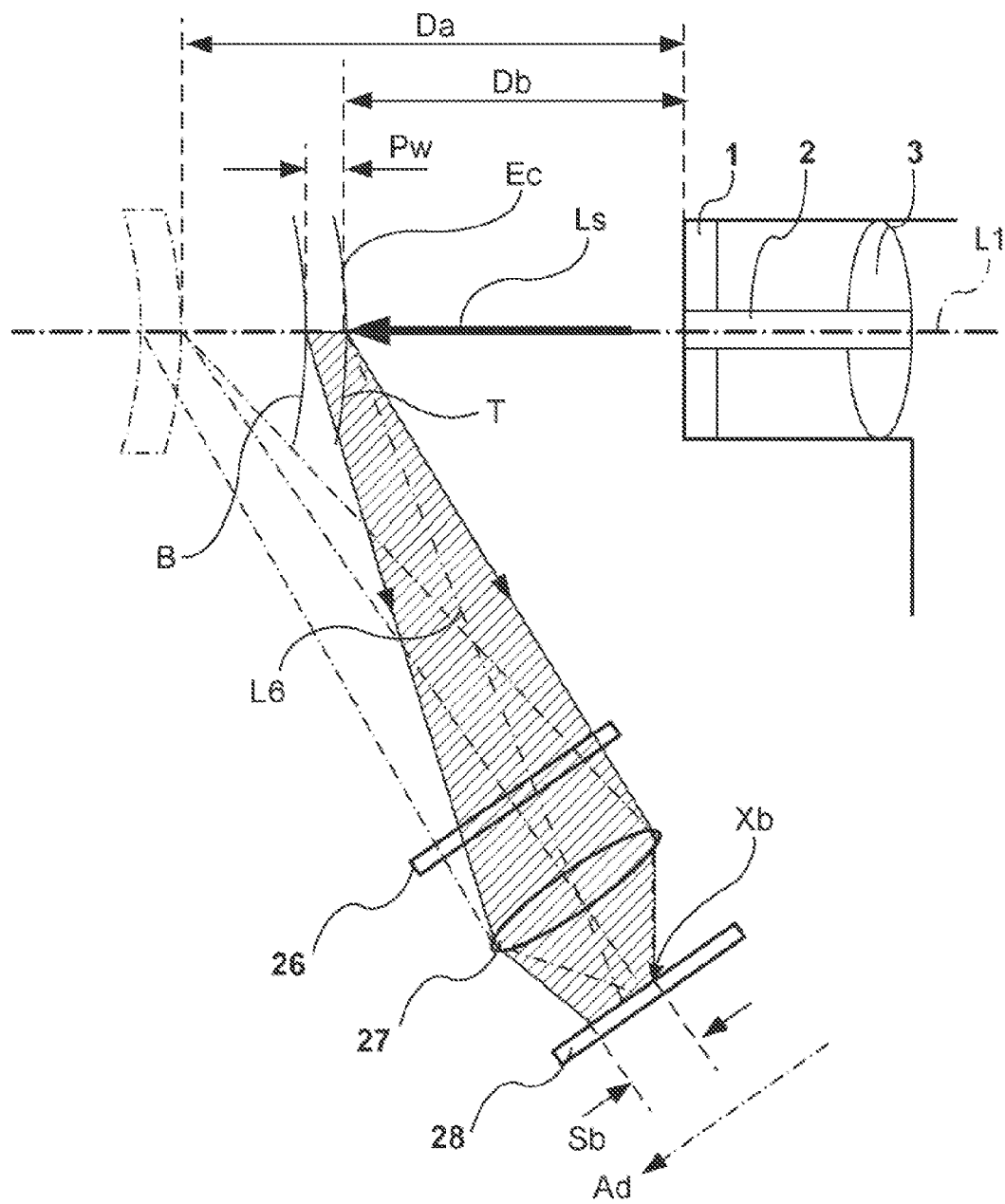
FIG. 5 is a view showing imaging of scattered light from the cornea Ec having a corneal curvature radius larger than the average onto the imaging element 28.
Figure 6:
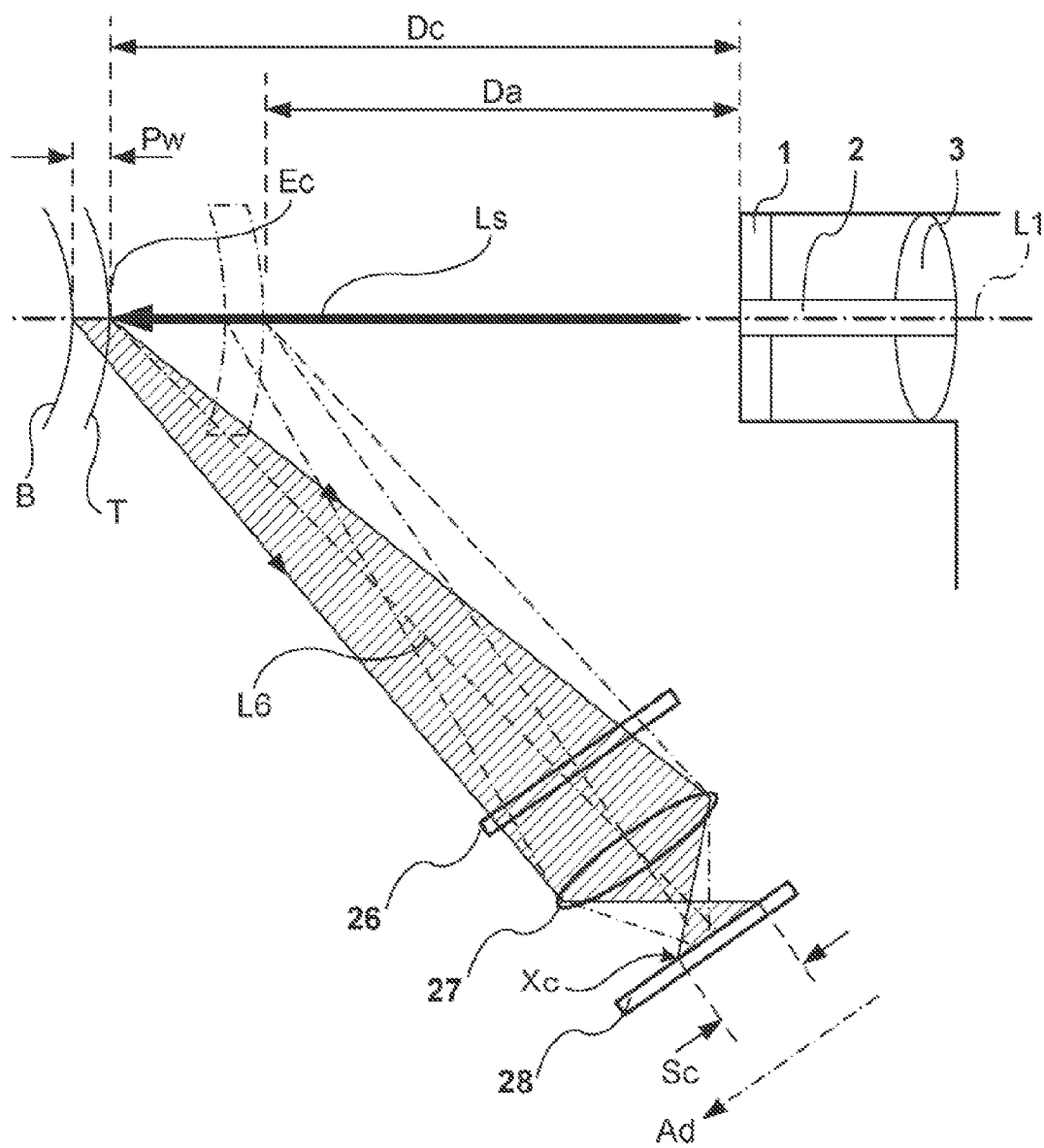
FIG. 6 is a view showing imaging of scattered light from the cornea Ec having a corneal curvature radius smaller than the average onto the imaging element 28.

FIGS. 4 to 6 are views each showing how scattered light of the cornea Ec from the LED light source 25 is formed into an image on the imaging element 28. Note that FIGS. 4 to 6 each show a portion near the corneal vertex of the cornea Ec, and show only components necessary for the following description. The same reference numerals as in FIG. 1 denote the same parts in FIGS. 4 to 6.

In addition, referring to FIGS. 4 to 6, corneal curvature radii R are different from each other. FIG. 4 shows a case in which the eye to be examined has the corneal curvature radius R which is average (a reference corneal curvature in optical system design). FIG. 5 shows a case in which the corneal curvature radius R is larger than the average. FIG. 6 shows a case in which the corneal curvature radius R is smaller than the average. Note that FIGS. 5 and 6 each show a case in which the corneal thickness measurement state shown in FIG. 4 is superimposed using chain lines. Referring to FIGS. 4 to 6, reference symbol Pw denotes a corneal thickness; T denotes the front surface of the cornea; B denotes the rear surface of the cornea; and Ls denotes illumination light from the nozzle 2 of the LED light source 25. Assume that the corneal thicknesses Pw shown in FIGS. 4 to 6 are the same in the three cases.

As described with reference to FIG. 3, in cornea bright spot alignment, the distance between the distal end portion of the nozzle 2 and the corneal vertex changes with changes in corneal curvature. Referring to FIGS. 4 to 6, the distance D between the corneal vertex of the cornea Ec and the distal end portion of the nozzle 2 after cornea bright spot alignment exhibits the relationship of Db<Da<Dc due to differences in the corneal curvature radius R. As a consequence, the angle of the optical axis L6 which receives scattered light from the cornea and the optical path length to the imaging element 28 vary, resulting in the occurrence of blur on an image on the imaging element 28.

Figure 7A:
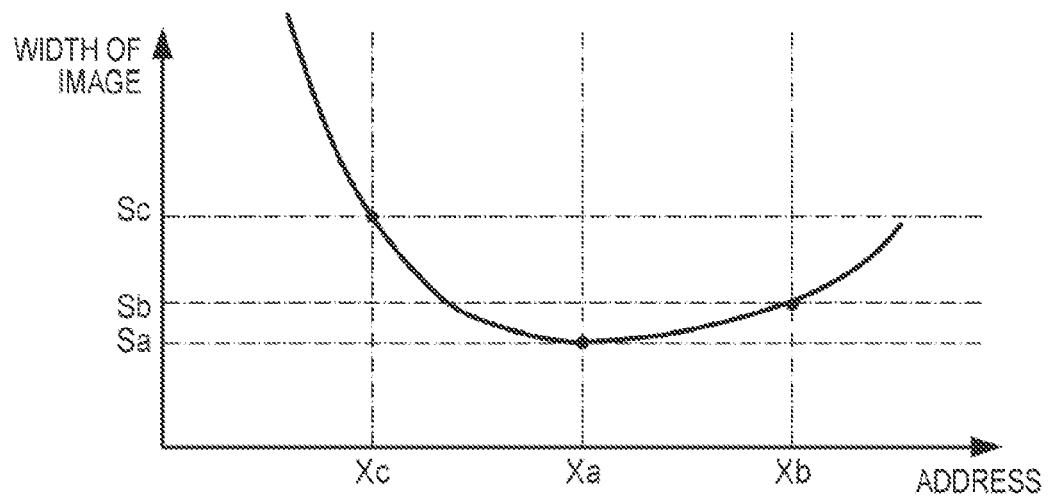
FIGS. 7A and 7B are graphs showing the relationship between the width of an image on an imaging element and the position of the image on the imaging element in a corneal thickness measurement optical system.

FIG. 7A shows the relationship between the widths of images on the imaging element 28 and the positions of the images in the case in which the corneal curvature radius R is average (FIG. 4), the case in which the corneal curvature radius R is larger than the average (FIG. 5), and the case in which the corneal curvature radius R is smaller than the average (FIG. 6). The abscissa in FIG. 7A represents the addresses of the positions of images on the imaging element 28 viewed in a direction Ad in FIGS. 4 to 6. Note that as positions Xa, Xb, and Xc of images, points at which scattered light from the corneal vertex of the cornea Ec, obtained by using the LED light source 25, are formed into images on the imaging plane of the imaging element 28 are used. FIGS. 4, 5, and 6 respectively show Xa, Xb, and Xc. The ordinate in FIG. 7A represents the widths of the images on the imaging element 28.

When the corneal curvature radius R of the eye to be examined is average, the position and width of the image are respectively Xa and Sa, and there is no blur in the image (FIG. 4). When the corneal curvature radius R of the eye to be examined is larger than the average, the position and width of the image are respectively Xb and Sb, and there is blur in the image (FIG. 5). When the corneal curvature radius R of the eye to be examined is smaller than the average, the position and width of the image are respectively Xc and Sc, and there is blur in the image (FIG. 6). As shown in FIG. 7A, therefore, the width of an image is large either when the corneal curvature radius R is large or when the corneal curvature radius R is small (Sb>Sa and Sc>Sa). When the corneal curvature radius R is large, the address of the position of the image is large (Xb>Xa). When the corneal curvature radius R is small, the address of the position of the image is small (Xc>Xa).

Upon receiving image data output from the imaging element 28, the corneal thickness calculation unit 31 reads the width of the image and the address of the position of the image described above. On the other hand, the corneal thickness correction data unit 32 stores correction values for the widths of images corresponding to addresses. For example, the corneal thickness correction data unit 32 has a correction value table holding the positions of the images captured by the imaging element 28 in the light receiving optical system for corneal thickness measurement in correspondence with correction values. The corneal thickness calculation unit 31 acquires a correction value from the corneal thickness correction data unit 32 (for example, the correction value table) by using the position of an image which indicates a corneal thickness (step S923). The corneal thickness calculation unit 31 then corrects the width of the image read from the imaging element 28 by using the width of the image read from the imaging element 28 and the correction value for the width of the image which is read from the corneal thickness correction data unit 32 (step S924). Note that the width of an image may be measured by measuring the size of the image read from the imaging element 28 upon binarization with a proper threshold. The corneal thickness calculation unit 31 notifies the control unit 29 of the measurement value of the corneal thickness corrected in this manner (step S925).

Assume that the corneal thickness calculation unit 31 has received the image data output from the imaging element 28 and acquired Xb as the position (the address on the imaging element 28) of the image corresponding to the corneal thickness. This is the case in which the corneal curvature radius R is larger than the average. In this case, the corneal thickness calculation unit 31 reads a correction value corresponding to the address Xb of the image from the corneal thickness correction data unit 32. When calculating the corneal thickness, the corneal thickness calculation unit 31 acquires Sa/Sb as a correction value, and corrects the corneal thickness acquired from the above image data by using the correction value. For example, the corneal thickness correction data unit 32 has a correction value data table like that shown in FIG. 7A. The corneal thickness calculation unit 31 uses, as a correction value, the value (Sa/Sb) obtained by dividing Sa at the address Xa by Sb acquired in accordance with the address Xb. The corneal thickness calculation unit 31 obtains a corneal thickness after correction by multiplying the corneal thickness measured from the image data by the correction obtained in this manner.

Assume that the corneal curvature radius R is smaller than the average, and the corneal thickness calculation unit 31 has acquired Xc as the address of the position of an image corresponding to a corneal thickness from the image data output from the imaging element 28. In this case, the corneal thickness calculation unit 31 reads a correction value corresponding to the address Xc of the position of the image from the corneal thickness correction data unit 32. When calculating the corneal thickness, the corneal thickness calculation unit 31 acquires Sa/Sc as a correction value, and corrects the corneal thickness acquired from the above image data by using the correction value. For example, the corneal thickness calculation unit 31 uses, as a correction value, the value (Sa/Sc) obtained by dividing Sa at the address Xa by Sc acquired from a correction value data table like that shown in FIG. 7A in accordance with the address Xc. The corneal thickness calculation unit 31 obtains a corneal thickness after correction by multiplying the corneal thickness measured from the image data by the correction obtained in this manner.

Figure 7B:
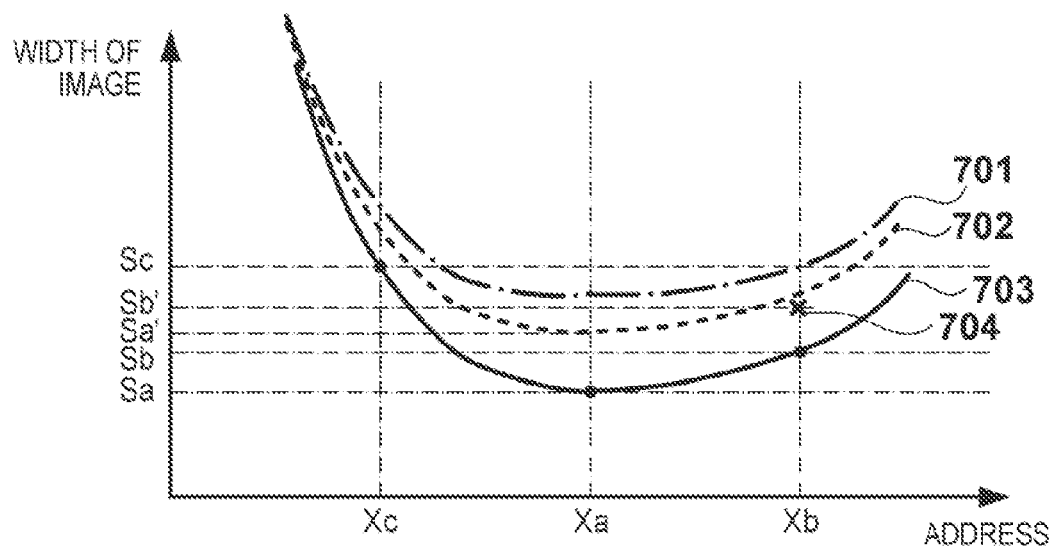

According to the above description, a correction value is calculated by using one kind of characteristic like that shown in FIG. 7A. However, the present invention is not limited to this. For example, as shown in FIG. 7B, it is possible to prepare a plurality of kinds of characteristic values (characteristic curves 701, 702, and 703 in FIG. 7B) and obtain a correction value by selecting the most suitable characteristic curve based on the actually measured position and width of an image. Assume that in the case shown in FIG. 7B, the position of the image is Xb, and the width of the image is indicated by an X mark 704. In this case, the characteristic curve 702 nearest to this measurement value is selected, and a correction value is obtained by using a value (Sb') at Xb of the characteristic curve 702 and a value (Sa') at Xa.

In the above manner, the corneal thickness calculation unit 31 corrects the width of the image, and calculates the corneal thickness Pw of the eye to be examined from the width of the image after correction, the imaging magnification of the lens, and the like. According to the above arrangement for corneal thickness measurement, correcting the widths of detected images by using correction values corresponding to the detected positions of the images can make the images corresponding to the corneal thicknesses of the eyes to be examined have the same width regardless of the corneal curvatures as long as the eyes have the same corneal thickness.

Although the ophthalmologic apparatus having both the function of measuring the corneal thickness of the eye to be examined and the function of measuring the eye pressure has been exemplified, the present invention may be an ophthalmologic apparatus having only the function of measuring the corneal thickness of the eye to be examined. When the present invention is to be applied to an ophthalmologic apparatus having only the function of measuring the corneal thickness of the eye to be examined, the apparatus may have an arrangement obtained by omitting the plane parallel glass 1, the nozzle 2, the air chamber 4, the observation window 5, the piston 7, the pressure sensor 8, the solenoid 34, the aperture 17, and the light receiving element 18 from the arrangement of the above embodiment.

As described above, in the ophthalmologic apparatus having at least the function of measuring the corneal thickness of the eye to be examined, the second alignment optical system (the projection system/light receiving system for cornea bright spot alignment) and the projection optical system for corneal thickness measurement are mainly formed along the optical axis L1. In addition, the light receiving optical system for corneal thickness measurement can be mainly formed along the optical axis L6. This makes it possible to form a corneal thickness measuring apparatus using an optical system with a simple arrangement. In addition, performing corneal thickness measurement by using cornea bright spot alignment will cause blur in an image on the imaging element 28 due to the differences in corneal curvature between the eyes to be examined at the time of corneal thickness measurement, resulting in errors in the measurement values of corneal thicknesses. According to the embodiment described above, however, it is possible to obtain accurate corneal thicknesses by correcting the measurement values of corneal thicknesses based on the positions of images on the imaging element 28. That is, the embodiment described above allows the ophthalmologic apparatus having the function of measuring corneal thickness to simplify the arrangement of the optical system and implement more accurate corneal thickness measurement.

In the ophthalmologic apparatus having both the function of measuring the corneal thickness of the eye to be examined and the function of measuring the eye pressure, the second alignment optical system, the projection optical system for corneal thickness measurement, and the eye pressure measurement optical system (the projection system/light receiving system for eye pressure measurement) can be mainly formed along the optical axis L1. In addition, as described above, the light receiving system for corneal thickness measurement can be mainly formed along the optical axis L6. This makes it possible to measure both a corneal thickness and an eye pressure by using the two functions with an optical system with a simple arrangement.

When calculating the eye pressure value of the eye E, it is possible to correct the eye pressure value by using a calculation result on corneal thickness. This can provide an ophthalmologic apparatus which can obtain an accurate eye pressure value with a simple optical system.

Although the above embodiment has exemplified the arrangement in which the optical axis L6 is placed in the direction obliquely below the eye E, the optical axis L6 can be placed at any position facing the eye E outside the optical axis L1. That is, the corneal thickness measurement optical system (the filter 26, the imaging lens 27, and the imaging element 28) may be configured so as to set its optical axis at a predetermined angle relative to the optical axis L1.

Note that the control unit 29 and the corneal thickness calculation unit 31 implement processing like that shown in FIG. 9 by, for example, causing a CPU to execute a predetermined program. However, the control unit 29 and the corneal thickness calculation unit 31 may be implemented by one CPU. In addition, part or all of the processing executed by the control unit 29 and/or the corneal thickness calculation unit 31 may be implemented by dedicated hardware or logic circuits.

In the above embodiment, the control unit 29 performs cornea bright spot alignment by itself. However, the user may perform alignment by moving the apparatus main body while watching a monitor displaying cornea bright spots.

Second Embodiment

The second embodiment will be described next. Recently, with the downsizing of imaging elements, the lenses of imaging optical systems have become smaller in size, resulting in restrictions in terms of lens fabrication and shorter back focus. This makes it difficult to implements a lens arrangement. In addition, a reduction in lens size will make it harder to set a large distance between aperture stops in an apparatus designed to perform alignment based on the positional relationship between two images obtained by capturing reflection images of the cornea using an alignment index through the two aperture stops in two directions. It is necessary to make light beams captured by the aperture stops enter the imaging lens. If, therefore, a large distance cannot be set between the aperture stops, it is impossible to maintain high alignment accuracy.

Japanese Patent Laid-open No. 2000-060801 has proposed to provide an alignment index projection system and a light receiving optical system outside an optical axis. The technique disclosed in Japanese Patent Laid-open No. 2000-060801 detects the imaging position of the light, regularly reflected by the cornea of the eye to be examined upon projection of an alignment index on the cornea, on the sensor provided in the light receiving optical system, and performs alignment of the distance (operation distance) from the cornea of the eye to be examined to the apparatus based on the shift amount between the detected imaging position and a reference position. This arrangement, however, requires an optical system for alignment, and hence the apparatus increases in size. The second embodiment will exemplify an alignment optical system which prevents the apparatus arrangement from being complicated even with reductions in the sizes of an imaging element and imaging lens, and is free from a deterioration in alignment performance.

FIG. 10A is a view showing an extracted portion including a prism stop 11, an imaging lens 12, and an imaging element 13 on an optical axis L1. The solid lines in FIG. 10A indicate a case in which the eye to be examined and a measuring unit are at a proper distance (d=WD) from each other. Note that reference symbol Ec denotes the cornea of the eye to be examined; and Ei denotes the reflection image formed by making the above alignment index projection system project an LED light source 21 as an alignment index on the cornea. For the sake of simplicity, an illustration of a plane parallel glass 1, the nozzle 2, the objective lens 3, the air chamber 4, and the observation window 5, which exist on the optical axis L1, is omitted.

The apparatus is designed to make the focal length of the objective lens 3 almost coincide with a reflection image position when the distance between the cornea of the eye to be examined and the measuring unit in the optical axis direction is set to the normal distance (d=WD). Therefore, a light beam passing through the objective lens becomes almost parallel light. A prism deflects the light beam. Light beams passing through the upper and lower aperture stops of the prism stop 11 form images on the imaging element 13 through the imaging lens 12. The imaging element 13 is placed at a position almost coinciding with the focal length of the imaging lens 12.

At this time, the monitor displays the images obtained by the imaging element 13, as shown in FIG. 11A. Reflection images T1 and T2 which have passed through the upper and lower aperture stops and are deflected by the prism are arranged in a line on an x-plane including an optical axis. On the other hand, the dotted lines indicate light beams when the above distance shifts from WD and increases (d>WD). Since the object points (cornea reflection images) become more distance when viewed from the measuring unit, the imaging element 13 forms the light beams into images between the imaging lens 12 and the imaging element 13. As a result, the reflection images T1 and T2 on the imaging element 13 become blurred images, which become point-symmetric with respect to the optical axis shown in FIG. 11B.

When the distance between the cornea of the eye to be examined and the measuring unit in the optical axis direction changes from the normal distance (WD), the two reflection images shift in the opposite directions. This is because, since light beams passing through the two aperture stops are deflected by prisms 11a and 11b at some angles, a change in WD will change the intersection positions between the imaging element 13 and the light beams. The ophthalmologic apparatus disclosed in the present invention performs alignment by using this principle.

Figure 2C:
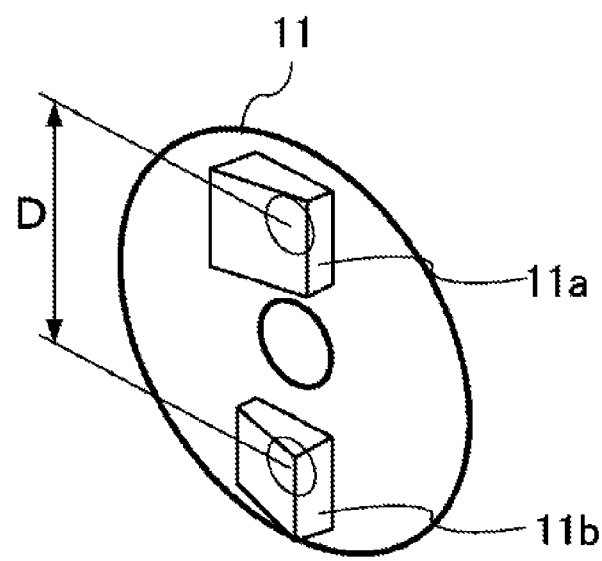
FIG. 2C is a view showing a distance D between aperture stops.

The accuracy of the imaging element 13 in the optical axis direction is determined by a distance D between two aperture stops shown in FIG. 2C, assuming that the number of pixels is constant relative to the sensor size. In order to explain how the resolution in the WD distance direction changes depending on the size of the lens diameter, FIG. 10B shows light beams in solid lines when an imaging lens 36 with a small lens size is used, and light beams in dotted lines when the imaging lens 12 with a lens size described with reference to FIG. 10A is used. A prism aperture 11' is designed to set a short distance (D' in FIG. 10B) between aperture stops to make light beams enter a small lens. Reducing the distance D between the upper and lower aperture stops of the prism stop 11 will reduce the angles at which reflection image light beams emerge from the stop apertures with respect to a slight change in WD. This reduces changes in the angles, and hence also reduces the moving amounts of the reflection images on the imaging element 13, resulting in a deterioration in alignment accuracy.

FIG. 10C shows an example in which optical members 37 made of, for example, a resin and respectively having two total reflection mirrors attached at almost 45° are arranged on the prism stop 11 to cope with an optical system which is reduced in size while the distance D between the aperture stops is maintained. The optical members 37 are provided on the optical paths of light beams passing through the aperture stops. Referring to FIG. 10C, the distance D between the aperture stops of the prism stop 11 is the same as that in the case of the imaging lens 12 in FIG. 10A. However, this arrangement uses the imaging lens 36 and an imaging element 13' reduced in size after the prism stop 11.

The optical members 37 offset light beams, captured by the prism stop 11 with the distance D between the aperture stops, to the optical axis sides. Reducing the distance between the light beams, which corresponds to the distance D between the aperture stops, in this manner allows the light beams to enter the imaging lens 36 reduced in size while maintaining the distance D between the aperture stops. Note that the optical members 37 have sizes that completely cover the apertures at the two ends of the prism stop 11 so as not to vignette the light beams deflected by the prisms 11a and 11b. In addition, the distance between the aperture stops is the distance that prevents a principal ray from being blocked by the nozzle 2 for blowing air against the cornea of the eye to be examined, and the optical members 37 change the optical paths of light beams so as to shorten the distance between the light beams passing through the aperture stops.

Although the prisms 11a and 11b, the aperture stops of the prism stop 11, and the optical members are sequentially arranged in the order named in the second embodiment, the present invention is not limited to this. For example, as shown in FIG. 12A, two aperture stops 11' having the distance D between them without any prism, the optical members 37, and prisms 11a' and 11b' may be sequentially arranged in the order named. That is, it is possible to use a structure having the prisms 11a' and 11b' as deflection units arranged on the exit sides of the optical members 37.

The prisms 11a' and 11b' have shapes similar to those of the prisms 11a and 11b, and function to deflect light beams. Although the optical members 37 provided at the respective aperture stops may be arranged as discrete components as shown in FIG. 12A, the two optical members 37 to be arranged at upper and lower positions may be integrally molded as shown in FIG. 12B.

As described above, the second embodiment allows a reduction in the sizes of the imaging element and imaging lens without complicating the apparatus arrangement or degrading the alignment performance.

According to the present invention, the ophthalmologic apparatus having the function of measuring the corneal thickness of the eye to be examined can accurately measure the corneal thickness with an optical system having a simple arrangement.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2011-040844, filed Feb. 25, 2011 and 2012-021344, filed Feb. 2, 2012, which are hereby incorporated by reference herein in their entirety.

What is claimed is:
1. An ophthalmologic apparatus comprising:
an imaging unit configured to image a cross-section of a cornea of an eye to be examined based on return light from the eye illuminated with corneal thickness measurement light;
a measurement unit configured to measure a corneal thickness from a cornea cross-sectional image of the eye imaged by said imaging unit;
a correction value obtaining unit configured to obtain a correction value corresponding to an error in the mea- sured corneal thickness, the error being generated in accordance with a curvature radius of the cornea, based on a characteristic curve;

a correction unit configured to correct the measured corneal thickness based on the obtained correction value.

2. The apparatus according to claim 1, wherein said correction value obtaining unit refers to a table that holds values corresponding to each of positions on the imaging plane of said imaging unit, and obtains a value corresponding to the position of the cornea cross-sectional image as the correction value.

3. The apparatus according to claim 1, wherein the position of the cornea cross-sectional image is a position at which the return light from a vertex of the cornea is formed into an image on the imaging plane of said imaging unit.

4. The apparatus according to claim 1, wherein a corneal thickness corrected by said correction unit is not more than a corneal thickness measured by said measurement unit.

5. The apparatus according to claim 1, further comprising:
an alignment imaging unit configured to image an alignment index on the cornea as a cornea reflection image using an imaging plane different from the imaging plane of said imaging unit; and
a positioning unit configured to perform positioning between the eye to be examined and a measurement unit including said imaging unit and said alignment imaging unit, based on the cornea reflection image,
wherein said measurement unit measures the corneal thickness after completion of the positioning.

6. The apparatus according to claim 5, wherein said imaging unit comprises:
an alignment optical system which projects the alignment index to the cornea of the eye;
a corneal thickness measurement optical system which projects the corneal thickness measurement light to the cornea of the eye and has a portion of said alignment optical system in common; and
a light receiving optical system which forms an image of the return light, from the cornea, of the corneal thickness measurement light projected to the cornea by said corneal thickness measurement optical system,
wherein said imaging unit images the cross-section of the cornea using an image of the return light formed by said light receiving optical system.

7. The apparatus according to claim 6, further comprising:
an eye pressure measurement optical system which has a portion of said alignment optical system in common, projects eye pressure measurement light for measuring an eye pressure of the eye to the eye, and detects reflected light of the eye pressure measurement light from the cornea;
a blowing unit configured to deform the cornea by blowing an air current against the cornea of the eye; and
a unit configured to measure an eye pressure value by correcting, using a corneal thickness corrected by said correction unit, an eye pressure value obtained based on a change in reflected light from said eye pressure measurement optical system in correspondence with deformation of the cornea by said blowing unit.

8. The apparatus according to claim 6, wherein said alignment optical system projects the alignment index onto the cornea substantially from a front of the cornea,
wherein said light receiving optical system forms an image of scattered light as the return light, from the cornea, of the corneal thickness measurement light projected to the cornea by said corneal thickness measurement optical system, and wherein said imaging unit images the cross-section of the cornea using an image of the scattered light formed by the light receiving optical system.

9. The apparatus according to claim 1, wherein the error is larger as a difference between a curvature radius of the cornea of the eye to be examined and a curvature radius of a cornea of an average eye is larger.

10. The apparatus according to claim 1, wherein the correction value obtaining unit is configured to obtain the correction value based on the characteristic curve and a position of the cornea cross-sectional image on an image plane of said imaging unit.

11. The apparatus according to claim 10, wherein the characteristic curve indicates a relationship between the position and thickness of the cornea cross-sectional image.

12. A control method for an ophthalmologic apparatus having an imaging unit configured to image a cross-section of a cornea of an eye to be examined based on return light from the eye illuminated with corneal thickness measurement light, the method comprising the steps of:
measuring a corneal thickness from the cornea cross-sectional image of the eye imaged by the imaging unit;
obtaining a correction value corresponding to an error in the measured corneal thickness, the error being generated in accordance with a curvature radius of the cornea, based on a characteristic curve; and
correcting the measured corneal thickness based on the obtained correction value.

13. A non-transitory computer-readable storage medium storing a program for causing a computer to execute steps in a control method for an ophthalmologic apparatus defined in claim 12.

14. The method according to claim 12, wherein in the step of obtaining the correction value, a table that holds values corresponding to each of positions on the imaging plane of the imaging unit is referred to, and a value corresponding to the position of the cornea cross-sectional image is obtained as the correction value.

15. The method according to claim 12, further comprising a step of performing positioning between the eye to be examined and a measurement unit including the imaging unit and an alignment imaging unit, based on a cornea reflection image which the alignment imaging unit obtains by imaging an alignment index on the cornea using an imaging plane different from the imaging plane of the imaging unit,
wherein, in the step of measuring, the corneal thickness is measured after completion of the positioning.

16. The method according to claim 12, wherein in the correction value obtaining step, the correction value is obtained based on the characteristic curve and a position of the cornea cross-sectional image on an image plane of the imaging unit.

17. The method according to claim 16, wherein the characteristic curve indicates a relationship between the position and thickness of the cornea cross-sectional image.

18. A processing apparatus comprising:
a corneal thickness obtaining unit configured to obtain a corneal thickness from a cornea cross-sectional image of an eye to be examined, which an imaging unit images based on return light from the eye illuminated with corneal thickness measurement light;
a correction value obtaining unit configured to obtain a correction value corresponding to an error in the measured corneal thickness, the error being generated in accordance with a curvature radius of the cornea, based on a characteristic curve; and a correction unit configured to correct the obtained corneal thickness based on the obtained correction value.

19. The apparatus according to claim 18, wherein said correction value obtaining unit refers to a table that holds values corresponding to each of positions on the imaging plane of the imaging unit, and obtains a value corresponding to the position of the cornea cross-sectional image as the correction value.

20. The apparatus according to claim 18, wherein the correction value obtaining unit is configured to obtain the correction value based on the characteristic curve and a position of the cornea cross-sectional image on an image plane of said imaging unit.

21. The apparatus according to claim 20, wherein the characteristic curve indicates a relationship between the position and thickness of the cornea cross-sectional image.

22. A processing method comprising the steps of:
obtaining a corneal thickness from a cornea cross-sectional image of an eye to be examined, which an imaging unit images based on return light from the eye illuminated with corneal thickness measurement light;
obtaining a correction value corresponding to an error in the measured corneal thickness, the error being generated in accordance with a curvature radius of the cornea, based on a characteristic curve; and
correcting the obtained corneal thickness based on the obtained correction value.

23. The method according to claim 22, wherein in the step of obtaining the correction value, a table that holds values corresponding to each of positions on the imaging plane of the imaging unit is referred to, and a value corresponding to the position of the cornea cross-sectional image is obtained as the correction value.

24. A non-transitory computer-readable storage medium storing a program causing a computer to execute the steps of the method according to claim 22.

25. The method according to claim 22, wherein in the correction value obtaining step, the correction value is obtained based on the characteristic curve and a position of the cornea cross-sectional image on an image plane of the imaging unit.

26. The method according to claim 25, wherein the characteristic curve indicates a relationship between the position and thickness of the cornea cross-sectional image.

* * * * *